(12) United States Patent
Hajianpour

(10) Patent No.: US 8,075,560 B2
(45) Date of Patent: Dec. 13, 2011

(54) EXTERNAL FIXATOR FOR DISTAL RADIUS FRACTURE

(75) Inventor: Mohammed A. Hajianpour, Fort Lauderdale, FL (US)

(73) Assignee: Nutek Orthopaedics, Inc., Fort Lauderdale, FL (US)

( * ) Notice: Subject to any disclaimer, the term of this patent is extended or adjusted under 35 U.S.C. 154(b) by 518 days.

(21) Appl. No.: 12/235,914

(22) Filed: Sep. 23, 2008

(65) Prior Publication Data

US 2010/0076434 A1 Mar. 25, 2010

(51) Int. Cl.
*A61B 17/60* (2006.01)
(52) U.S. Cl. ........................................................ 606/59
(58) Field of Classification Search .............. 606/54–59, 606/90, 105, 282
See application file for complete search history.

(56) References Cited

U.S. PATENT DOCUMENTS

| | | | | |
|---|---|---|---|---|
| 4,244,360 A | * | 1/1981 | Dohogne | 606/59 |
| 4,693,240 A | * | 9/1987 | Evans | 606/54 |
| 5,078,719 A | * | 1/1992 | Schreiber | 606/87 |
| 5,304,177 A | * | 4/1994 | Pennig | 606/58 |
| 5,391,167 A | * | 2/1995 | Pong et al. | 606/57 |
| 5,403,313 A | * | 4/1995 | Lin | 606/54 |
| 6,197,027 B1 | * | 3/2001 | Hajianpour | 606/59 |
| 6,585,736 B2 | * | 7/2003 | Hajianpour | 606/57 |
| 7,169,149 B1 | * | 1/2007 | Hajianpour | 606/54 |
| 2009/0118733 A1 | * | 5/2009 | Orsak et al. | 606/60 |

* cited by examiner

*Primary Examiner* — Eduardo C Robert
*Assistant Examiner* — Jerry Cumberledge
(74) *Attorney, Agent, or Firm* — Malin Haley DiMaggio Bowen & Lhota, P.A.

(57) ABSTRACT

An external fixator for a fractured distal radius including a first plurality of vertical passages for pins extending downward from a first pin mounting block into one or more bone fragments and one or more frame element apertures extending from an elongated frame element for pins extending downward from the device into the shaft of the radius. In addition, the elongated frame element includes a sliding pin slot with a sliding structure allowing a single pin to be moved to provide extension between the fragments and the shaft. A sliding internal plate including holes aligned with the first plurality of vertical passages is moved by a pair of setscrews to clamp the pins extending through the first plurality of vertical passages. The device also includes a second pin mounting block that extends downward parallel to the pins extending from first pin mounting block to hold pins directed laterally into the fragment(s).

10 Claims, 5 Drawing Sheets

EXTERNAL FIXATOR FOR DISTAL RADIUS FRACTURE

BACKGROUND OF THE INVENTION

1. Field of the Invention

This invention relates to devices for external fixation of fractured bones, and, more particularly, to an external fixator in which bone setting pins are clamped from a plurality of angles for fixation of multiple fragments of an end portion of a radius bone.

2. Description of the Related Art

The fracture of the distal radius is one of the most common human fractures, occurring in as many as 350,000 people per year in the United States alone. The conventional processes both for reducing such a fracture and for maintaining the bones in proper alignment during the subsequent healing process involves applying and maintaining an extension force across the fracture, with ligamental taxis being relied upon to hold the bones in place. The process for treating a fractured distal radius is described in the 1901 edition of Gray's Anatomy in the following manner, "The treatment consists of flexing the forearm, and making a powerful extension from the wrist and elbow, depressing at the same time the radial side of the hand, and retaining the parts in that position by well-padded pistol-shaped splints."

A common method for the treatment of a fractured distal radius involves the use of standard immobilizing cast techniques, preventing movement of the radiocarpal joint throughout the course of rehabilitation. A problem with this method is that it sometimes results in inadequate internal fixation, which can cause deformity, pain, and prolonged disability.

Another method for treating a fractured distal radius involves external pin fixation. This process involves the surgical insertion of skeletal traction pins on both sides of the fracture, with a frame being connected to the pins for immobilizing the bones, and for holding them together until the fracture is mended. Initial structures and methods for applying external pin fixation for the treatment of a fractured distal radius provide for the immobilization of the radiocarpal joint, so that the hand cannot be flexed. While this type of fixation often provides an improvement over conventional casting techniques in the management of severe fractures of the distal radius, immobilization of the radiocarpal joint during the treatment period typically results in a long period of stiffness and disability after the external fixation device is removed. Typically, the external fixation device is left in place during the healing process for six to eight weeks. After the fixation device is removed, three to six months are required for the patient to regain motion of his hand.

Subsequent structures and methods have been developed to provide adequate fixation during the healing process while allowing flexure in the radiocarpal joint. Using these newer structures and methods, patients have been able to gain immediate use of the joint after surgery.

An example of a fixation device and fixation method that provides adequate fixation and allows flexure in the radiocarpal joint is described in U.S. Pat. No. 6,585,736, the disclosure of which is incorporated herein by reference. U.S. Pat. No. 6,585,736, describes a fixation device that is configured to provide external fixation of a fractured distal radius by including a first number of holes for pins extending downward from the fixture into one or more bone fragments, rods that extend downward and hold pins laterally into one or more bone fragments, and a second number of holes for pins extending downward from the fixture into the shank of the radius. The fixture also includes a sliding block through which rods extend to hold pins directed laterally into the fragments. A sliding plate including a number of holes aligned with the first number of holes is moved by a pair of setscrews to clamp the pins extending through the first number of holes. The second number of holes includes a hole within a sliding structure allowing a single pin to be moved with a fixture to provide extension between the fragments and the shank of the radius.

What is needed is a simpler and more functionally effective structure and method for holding pins laterally into bone fragments. Since a plurality of individual rods have typically been used to secure fragments laterally, what is needed is a structure and method that will provide a more reinforced structure to hold the pins laterally. In addition, such a structure and method would preferably allow the laterally placed pins to be placed at a plurality of angles. Such a structure and method would still allow mobility of the hand and wrist while presenting fewer surfaces to get caught on other objects and being more cost effective due to it having fewer parts.

SUMMARY OF THE INVENTION

An external fixator comprising a fixator body, said fixator body having an elongated frame element at one end and a first pin mounting block at the opposite end. A second pin mounting block is orthogonally and slideably connected to one side of the fixator body. The external fixator provides a more stable structure to fix a plurality of fragments (or segments) of a fractured distal radius bone with respect to the radius bone shaft.

The fixator body comprises the elongated frame element at one end and the first pin mounting block at the opposite end of the fixator body. The fixator body is externally attached to the distal radius bone by two mounting pins and a sliding pin housed in the elongated frame, both screwed and locked into the radius bone shaft, above the radius bone and the wrist. The fixator body is thus mounted parallel to the radius bone and above the radius bone extending over the wrist area of the patient.

The first pin mounting block includes a somewhat rectangular or square body having a plurality of vertical parallel passages, each block passage sized to receive a vertical fragment pin vertically or downwardly in the direction of the distal radius bone and bone fragments to be pinned.

The second pin mounting block has one or more pin holding members, wherein each pill holding member contains a spherical pin holder (or locator) and is mounted in an elongated slot on the second pin mounting block. Each spherical pin holder allows a lateral fragment pin used to fix bone chips in place to be individually angularly disposed in a spherical angle of about thirty degrees from the perpendicular to the second pin mounting block surface and each lateral fragment pin can be screwed into a bone fragment and locked in place by tightening the pin holding member containing it. The second pin mounting block can also slide laterally (backwards and forwards in the same direction as the radius bone) for additional positioning of the horizontal fragment pins.

Because of the location of the first pin mounting block and the second mounting pin block and their orthogonal relationship, the distal radius bone fragments can be fixed in place in multiple dimensions.

The first pin mounting block uses a sliding internal plate with a plurality of holes that correspond to the first pin mounting block vertical passages for receiving the vertical fragment pin so that the vertical fragment pin can be firmly locked within a vertical passage by virtue of interaction with the holes and the vertical pin passages.

Using the present invention as an external fixator for a radius fracture allows for immediate post operative wrist and finger function and motion from dorsal to volar function, radial to ulnar deviation, supination, and pronation.

DETAILED DESCRIPTION OF THE INVENTION

Figure 1:
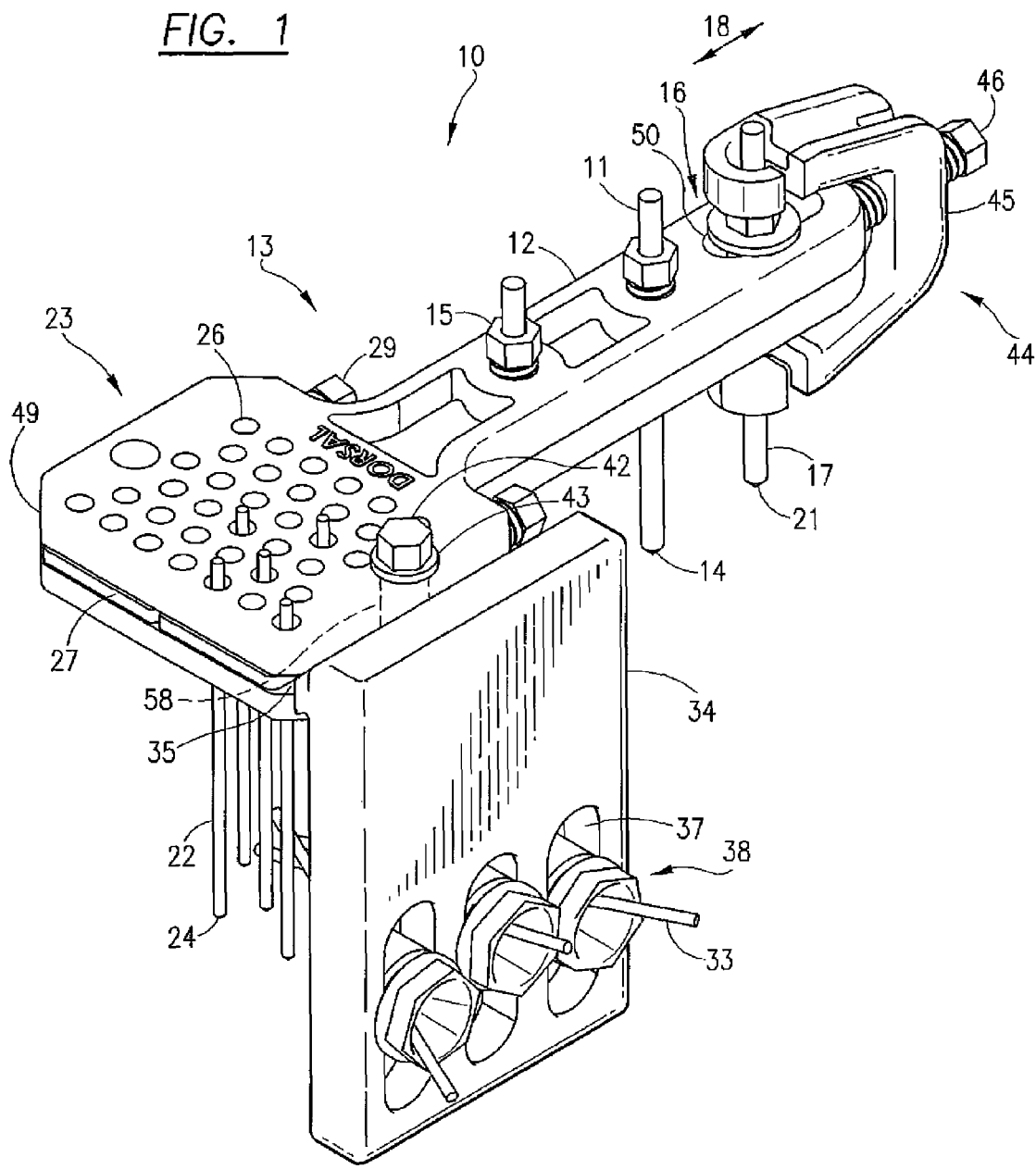
FIG. 1 is a perspective view of a device for external fixation.
Figure 2:
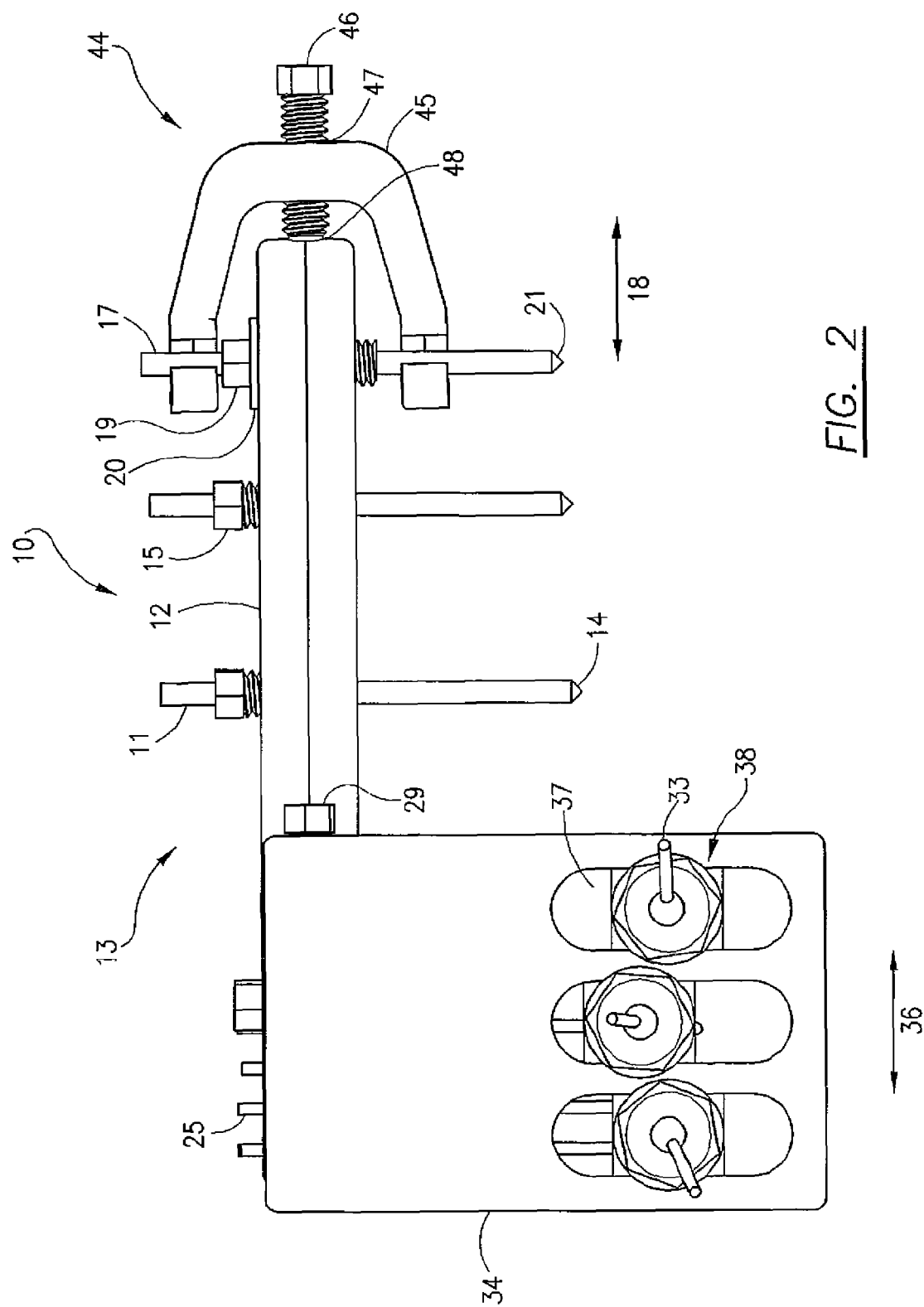
FIG. 2 is a front side elevational view of the device of FIG. 1.
Figure 3:
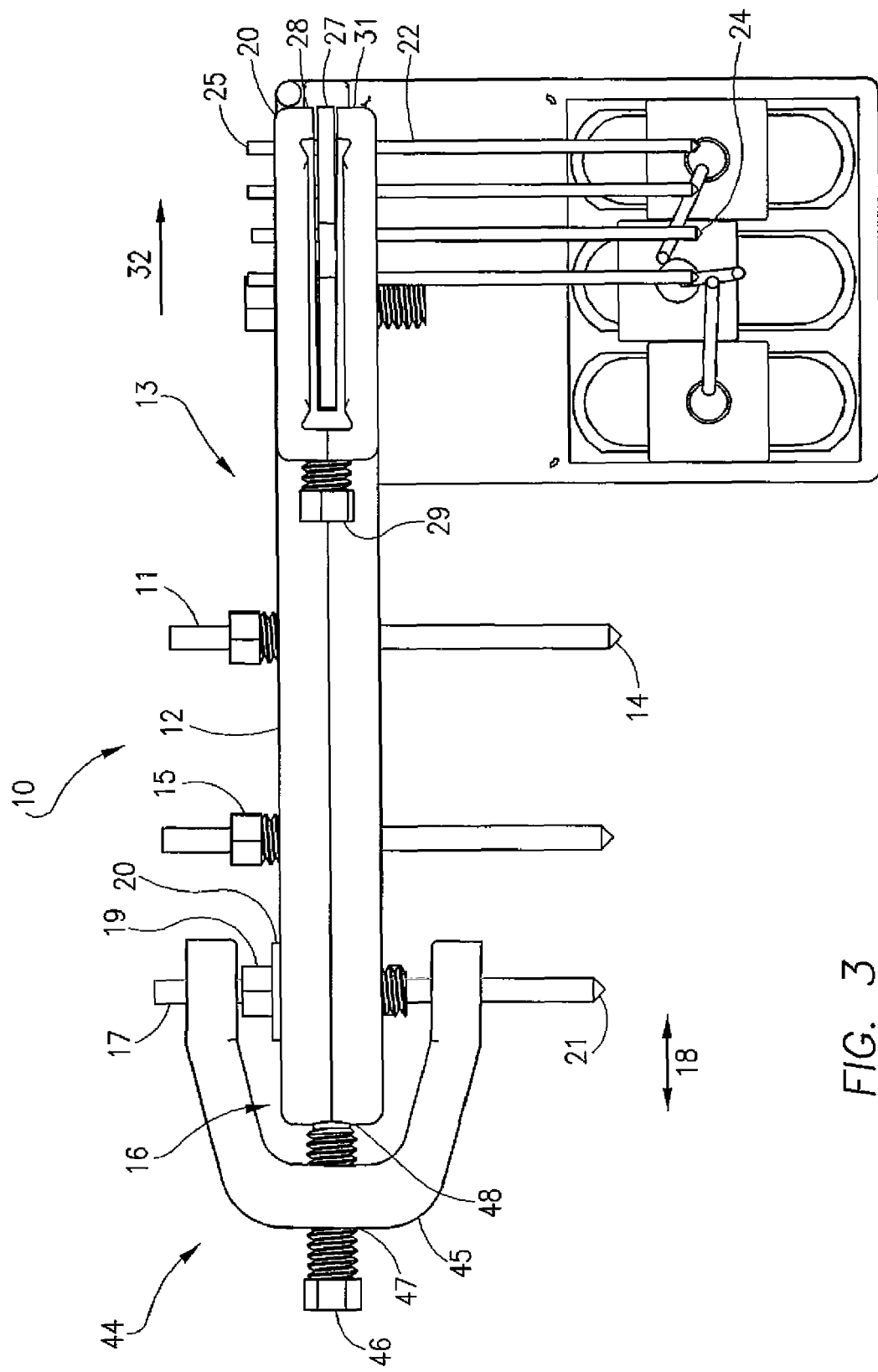
FIG. 3 is aback side elevational view of the device of FIG. 1.

An external fixator 10, built in accordance with the present invention, will now be described, with an initial reference to FIG. 1, FIG. 2, and FIG. 3. The external fixator 10 is configured for surgical attachment to the shank portion of a radius bone (not shown) by means of two mounting pins 11, extending downward from an elongated frame element 12 of a fixator body 13, with the pointed end 14 of each mounting pin 11 being screwed into the bone. In the elongated frame element 12, a pin clamping screw 15 is used to hold each mounting pin 11 in a fixed relationship with the fixator body 13. Each pin clamping screw 15 extends within an elongated frame element aperture in the elongated section and includes a number of flexible sections that move inward engaging the pin 11 extending through the pin clamping screw 15 as that pin clamping screw 15 is driven into engagement with said elongated frame element aperture. Near the proximal end 16 of the elongated frame element 12, a sliding pin 17 is first mounted to slide in the longitudinal directions of arrow 18 within an sliding pin slot 50, and then, after tightening, to be held in place within the fixator body 13 by means of a sliding pin clamping screw 19 and a nut 20. The sliding pin 17 is preferably identical to the mounting pins 11, including a pointed end 21 fastened into the bone shank. The sliding pin clamping screw 19, holding the sliding pin 17, while longer than the pin clamping screws 15, is otherwise similar to the pin clamping screws 15.

A removable extension-setting fixture 44, is configured to set a distance between the sliding pin 17 and other features of the external fixator 10. The extension-setting fixture 44 includes a frame 45 and a setscrew 46, which extends through a threaded hole 47 within the frame 45 to engage a proximal contact surface 48 of the fixator body 13.

The fragment or fragments of the fractured distal radius is/are held in place in part by a number of vertical fragment pins 22, extending downward from a first pin mounting block 23 of the fixator body 13. Each of the vertical fragment pins 22 includes a pointed end 24 for attachment within the bone fragment. If necessary, a portion 25 of vertical fragment pins 22 extending upward from the fixator body 13 are cut off after the vertical fragment pins 22 are fastened in place by a means of a plate driving mechanism.

The first pin mounting block 23 of the fixator body 13 is bifurcated, being divided to include a slot 28. As a result, the first pin mounting block 23 is divided into an upper portion 30 and a lower portion 31. In addition, a second pin mounting block 34 slides within a track 35 in the first pin mounting block 23 of the fixator body 13, being clamped in place by a block clamping screw 42 and a washer 43, which together serve as a plate clamping mechanism. The block clamping screw 42 extends through a clearance hole 58 in the first pin mounting block 23 that passes through the upper portion 30 of the first pin mounting block 23, and the lower portion 31 of the first pin mounting block 23.

The first pin mounting block 23 also has a pattern of vertical parallel passages 26, extending through both the upper portion 30 and the lower portion 31, for mounting the vertical fragment pins 22. The external fixator 10 also includes a sliding internal plate 27, sliding within the slot 28, and a pair of plate-adjusting screws 29. The sliding internal plate 27 includes a pattern of holes aligned with the vertical parallel passages 26 that extend through both the upper portion 30 and the lower portion 31 of the first pin mounting block 23. After the vertical fragment pins 22 to be used in a particular application of the external fixator 10 are inserted through the vertical parallel passages 26 and holes on the sliding internal plate 27, with these holes in alignment, the plate driving mechanism is actuated to simultaneously clamp all of the vertical fragment pins 22. The plate driving mechanism comprises the sliding internal plate 27 located within the slot 28 and a pair of plate-adjusting screws 29 and is actuate by using the plate-adjusting screws 29 to drive the sliding internal plate 27 in the direction of arrow 32, which simultaneously clamps all of the vertical fragment pins 22. After this is completed and the vertical fragment pins 22 are clamped in this way, the block clamping screw 42 is tightened, clamping the sliding internal plate 27 in place within the slot 28 and the second pin mounting block 34 rigidly in place in the track 35.

Figure 4:
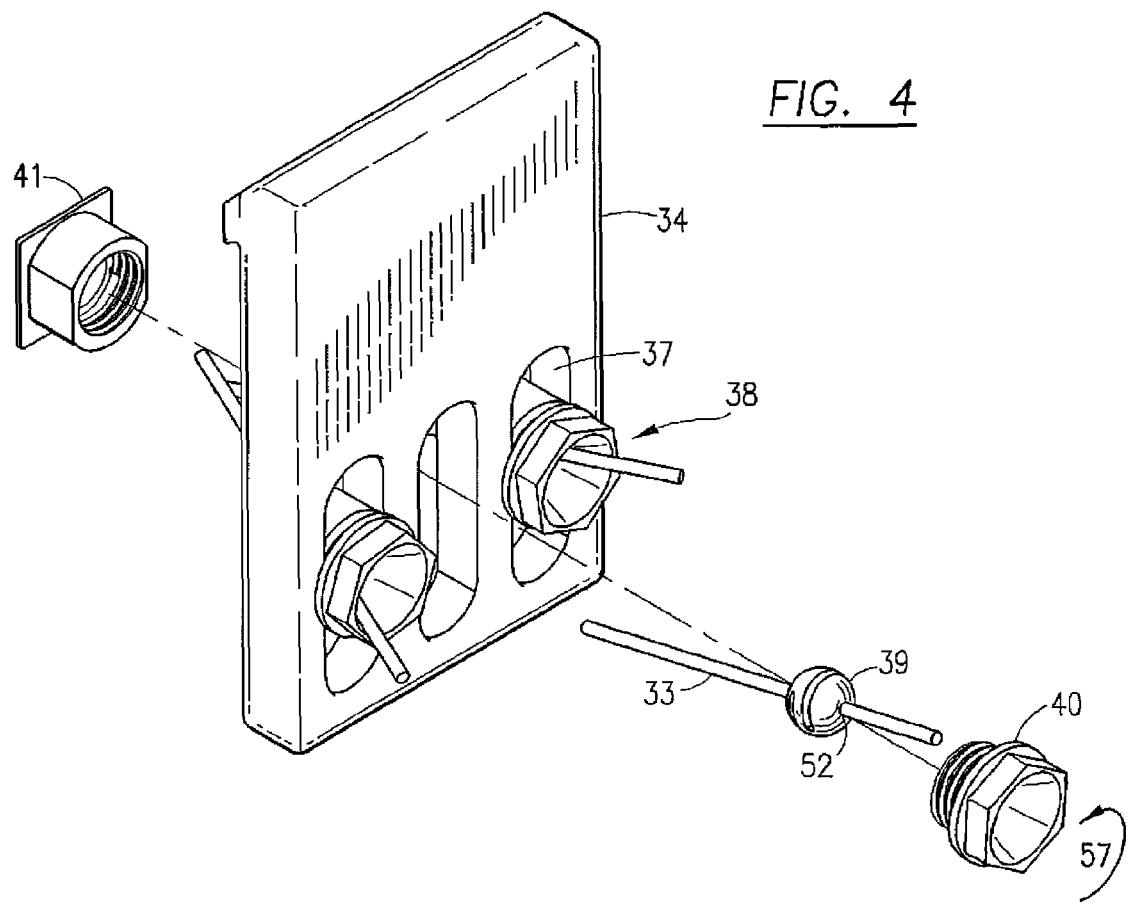
FIG. 4 is a perspective view of the side plate with an exploded perspective view of a pin mounting member of the device of FIG. 1.
Figure 5:
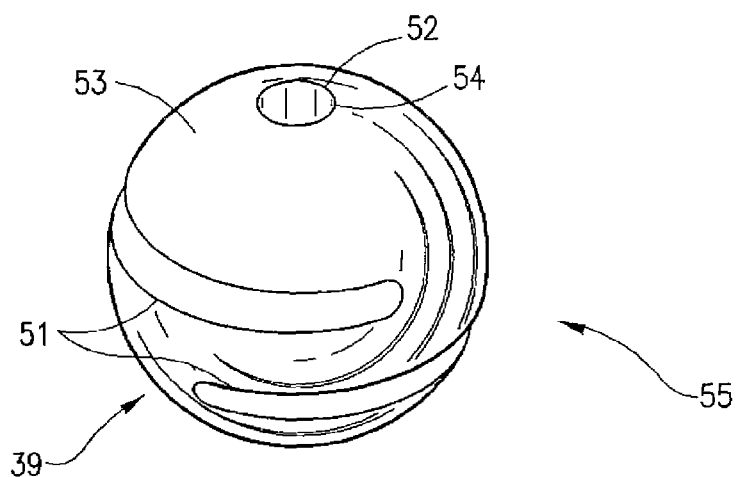
FIG. 5 is a perspective view of a spherical pin holder within the device of FIG. 1.
Figure 6:
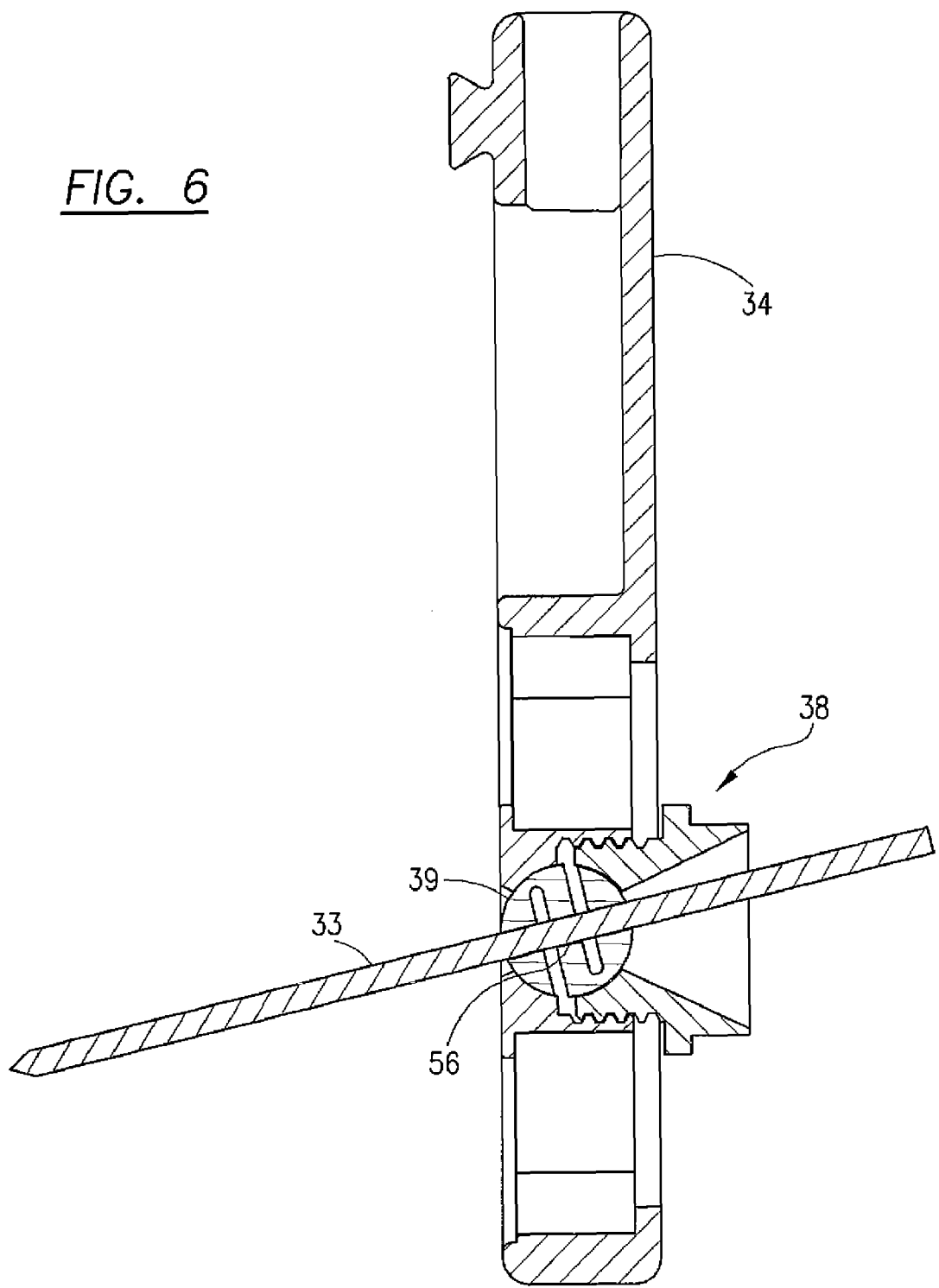
FIG. 6 is a cross sectional side phantom elevational view of the side plate of the device of FIG. 1.

Referring now to FIG. 4, FIG. 5, and FIG. 6, one or more bone fragments are also be held in place with one, two, or three lateral fragment pins 33, extending inward from the second pin mounting block 34. These lateral fragment pins 33 are similar or identical to the vertical fragment pins 22, before the vertical fragment pins 22 are cut off. The second pin mounting block 34 is held within a track 35 on the first pin mounting block 23 of the housing frame 11, and is mounted to slide in the longitudinal directions indicated by arrow 36. The second pin mounting block 34 has three elongated slots 37 that contain slidably mounted pin holding members 38. Each slidably mounted pin holding member 38 consists of a spherical pin holder 39 contained within an exterior clamping component 40 and an interior clamping component 41 that are releasably fastened together. In addition, each spherical pin holder 39 has a pin mounting hole 52 and a deformable portion 53. One lateral fragment pin 33 is mounted into each spherical pin holder 39 through its pin mounting hole 52, and is be clamped in place, when the exterior clamping component 40 and the interior clamping component 41 are tightened, which deflects the deformable portion 53. Each mounted pin holding member 38 can be adjusted vertically within the elongated slots 37 and each lateral fragment pin 33 can be angularly adjusted as much as thirty degrees from a central position in which the lateral fragment pin 33 extends perpendicularly from the second pin mounting block 34 within its spherical pin holder 39 in order to be positioned to provide the ideal angle for that lateral fragment pin 33 to properly hold the targeted bone fragment.

The spherical pin holder 39 includes a pair of ball slots 51 extending perpendicular to a pin mounting hole 52 inward across the pin mounting hole 52 and partly across the spherical pin holder 39, so that the deformable portion 53 is actuated between each end 54 of the pin mounting hole 52 and the ball slot 51 that is nearer to the end 54.

The pin mounting hole 52 extends through a center of the spherical pin holder 39, being divided by the ball slots 51 into a deflectable part 55 within each of the deformable portions 53 and a central part 56 extending between the ball slots 51. When the exterior clamping component 40 is tightened with the interior clamping component 41 by rotation in the direction of arrow 57 to increase an engagement force holding the spherical pin holder 39 in place, the deformable portions 53 are deflected inward, bring the deflectable parts 55 of the pin mounting hole 52 out of alignment with the central part 56 thereof, so that the lateral fragment pin 33 is clamped in place within the pin mounting hole 52. Then, when the clamping member is loosened by rotation opposite the opposite the direction of arrow 57 to decrease the engagement force holding the spherical pin holder 39 in place, the deformable portions 53 return outward, so that the deflectable parts 55 of the pin mounting hole 52 return into alignment with the central part 56 thereof, allowing movement of the lateral fragment pin 33 within the pin mounting hole 52 and movement of the spherical pin holder 39 within the exterior clamping component 40 and the interior clamping component. For example, the lateral fragment pin 33 may be rotated as much as thirty degrees from a central position in which the lateral fragment pin 33 extends perpendicularly from the second pin mounting block 34.

The configuration shown in the figures is assembled particularly for treating a distal fracture of the right radius. For treating a distal fracture of the left radius, the lateral fragment pins 33 are arranged to extend inward from the opposite side of the external fixator 10 by mounting the second pin mounting block 34 in an alternate track 49, seen in FIG. 1, within the first pin mounting block 23.

A preferred method for installing the external fixator 10 to provide both support and extension to a fractured radius will now be explained. First, the sliding pin 17 is surgically inserted and driven into the shank portion of the radius, while the desired combination of vertical fragment pins 22 and lateral fragment pins 33 are surgically implanted and driven into the distal fragment or fragments of the radius. The order in which these pins 17, 22, 33 are implanted and driven may be arbitrary, or may be determined by surgical considerations including the exact type of the fracture. The relationship between the sliding pin 17 and the other pins driven into the fragments must be such that the sliding pin 17 can subsequently be slid within the sliding pin slot 50 opposite the direction of arrow 32. Next, the setscrew 46 is tightened to move the pins 22 and 33 away from the sliding pin 30, providing a level of extension needed to properly set the fracture. Then, the mounting pins 11 are surgically installed and driven into the radius. Finally, the setscrew 46 is loosened, and the extension-setting structure 44 is removed from the external fixator 10.

The pins 11, 17, 22, and 33 are preferably commercially available devices, which are conventionally composed of stainless steel. The frame 45 of the extension setting fixture 44 is preferably composed of aluminum. Other portions of the external fixator 10 are preferably composed of thermoplastic resins, with the screws being composed, for example, of nylon, and with the remaining parts being composed, for example, of polycarbonate. This use of thermoplastic materials makes it possible to form X-ray images of the bones through the external fixator 10. Furthermore, such materials provide a sufficient combination of strength and resiliency to allow a pattern of vertical fragment pins 22 to be clamped simultaneously as described above, in spite of dimensional variations between the patterns of holes holding the vertical fragment pins 22 in the sliding internal plate 27 and in the fixator body 13.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. An apparatus for external fixation of bone fragments, wherein said apparatus comprises:
   a fixator body comprising a first pin mounting block at one end that includes a plurality of vertical parallel passages providing positions for vertical fragment pins and an elongated frame element at an opposite end that includes elongated frame element apertures providing positions for mounting pins;
   a pair of mounting pins, for attachment of the distal radius bone, housed in said elongated frame;
   vertical fragment pins mounted in said first pin mounting block;
   a sliding plate mounted to slide along said fixator body, wherein said sliding plate includes holes aligned with said vertical parallel passages, providing positions for the vertical fragment pins that extend through said vertical parallel passages;
   a plate driving mechanism movable in an engagement direction to slide said sliding plate along said fixator body, simultaneously clamping the vertical fragment pins; and
   a second pin mounting block, slidably mounted orthogonally on one side of said fixator body, wherein said second pin mounting block extends in a direction parallel to said first pin mounting block, is moveable along an edge of said fixator body, and a second pin mounting block clamp connected to said fixator body and said second pin mounting block for clamping said second pin mounting block in place;
   wherein said second pin mounting block contains one or more vertically oriented elongated slots, each which contain a slidably mounted pin holding member comprising:
   a spherical pin holder containing a pin mounting hole, which provides a position for a lateral fragment pin to extend through said pin mounting hole towards said vertical fragment pins, and at least one deformable portion; and
   a spherical pin holder clamping mechanism comprising an exterior clamping component and an interior clamping component, releasably fastened together and engaging an internal mounting surface within said elongated slots, wherein said spherical pin holder clamping mechanism when tightened can deflect the deformable portion of each spherically rounded member to hold the side pin in place within the pin mounting hole.

2. The apparatus of claim 1, wherein:
   the first pin mounting block is bifurcated to form an upper section, a lower section, and a slot between said upper and lower sections,
   said sliding plate is mounted to slide in the slot between said upper and lower sections,
   said vertical parallel passages extend through said upper and lower sections, and
   said plate driving mechanism is actuated by sliding said sliding plate.

3. The apparatus of claim 2, wherein said plate clamping mechanism is actuated by tightening a block clamping screw and a washer.

4. The apparatus of claim 3, wherein said plate driving mechanism comprises a first plate-adjusting screw sliding said sliding plate along said fixator body.

5. The apparatus of claim 4, wherein said plate driving mechanism further comprises a second plate-adjusting screw sliding said sliding plate along said fixator body.

6. The apparatus of claim 1, wherein the elongated frame element includes a sliding pin slot.

7. The apparatus of claim 6, further comprising a sliding pin extending through said sliding pin slot, slidably mounted on said elongated frame element and releasably clamped in place on said elongated frame element, wherein
- sliding said sliding pin along the sliding pin slot in an extension increasing direction increases a distance between a said sliding pin and the vertical fragment pins, and
- said sliding pin is fastened within said sliding pin slot by tightening a sliding clamping screw and a nut, wherein said sliding clamping screw has threads engaging said nut.

8. The apparatus of claim 7, wherein said sliding clamping screw includes a number of flexible sections moving inward to engage said sliding pin as said sliding clamping screw is driven into engagement with said nut.

9. The apparatus of claim 6, further comprising one or more pin-clamping screws, wherein
- the elongated frame element apertures are comprised of internally threaded holes, said pin-clamping screw extends within said internally threaded hole, and
- said pin-clamping screw includes a number of flexible sections moving inward to engage said pin extending through said pin-clamping screw as said pin-clamping screw is driven into engagement with said internally threaded hole.

10. The apparatus of claim 1, wherein said lateral fragment pin, while the spherical pin holder clamping mechanism is not tightened, can be adjusted
- angularly up to thirty degrees from a position perpendicular to said second pin mounting block, and
- vertically to any position within the elongated slots in which the pin holding member is mounted.

* * * * *